United States Patent [19]
Aisaka et al.

[11] Patent Number: 6,153,419
[45] Date of Patent: *Nov. 28, 2000

[54] METHOD FOR QUANTITATIVE DETERMINATION OF 1,5-ANHYDROGLUCITOL

[75] Inventors: Kazuo Aisaka, Machida; Sakae Tazoe, Fuji; Katsuhiko Ando, Machida; Keiko Ochiai, Ebina, all of Japan

[73] Assignee: Kyowa Hakko Kogyo Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/930,709
[22] PCT Filed: Feb. 19, 1997
[86] PCT No.: PCT/JP97/00440
 § 371 Date: Oct. 16, 1997
 § 102(e) Date: Oct. 16, 1997
[87] PCT Pub. No.: WO97/31103
 PCT Pub. Date: Aug. 28, 1997

[30] Foreign Application Priority Data

Feb. 20, 1996 [JP] Japan .................................. 8-032393

[51] Int. Cl.$^7$ ................ C12N 9/24; C12Q 1/34
[52] U.S. Cl. .................. 435/200; 435/18; 435/100; 435/872
[58] Field of Search .............. 435/18, 200, 872, 435/100

[56] References Cited

U.S. PATENT DOCUMENTS

| | | | |
|---|---|---|---|
| 4,810,640 | 3/1989 | Nakamura et al. | 435/25 |
| 4,994,377 | 2/1991 | Nakamura et al. | 435/25 |
| 5,426,033 | 6/1995 | Kojima et al. | 435/14 |

FOREIGN PATENT DOCUMENTS

| | | |
|---|---|---|
| 0673999 | 9/1995 | European Pat. Off. . |
| 62-079780 | 4/1987 | Japan . |
| 63-185397 | 7/1988 | Japan . |
| 7-067697 | 3/1995 | Japan . |

OTHER PUBLICATIONS

Mega et al, J. Biochem. 94:1637–1647 (1983).
Segel, Biochemical Calculations, 2nd Ed., John Wiley & Sons, New York, pp. 246–273, 1976.
McBride et al, J. Bacteriol. 169(11): 5002–5007 (1987).
Kalf et al, J. Biol. Chem. 230: 691–698 (1958).
Hey et al, J. Bacteriol. 96(1): 105–110 (1968).
Journal of Analytical Bio–Science, vol. 19, No. 2 (1996) 121–127.
Appl. Biochem. Biotechnol., vol. 56, No. 3 (1996) 301–310.
Japan Society of Clinical Chemistry, vol. 1, No. 1 (1994) 7–13.

*Primary Examiner*—Francisco Prats
*Attorney, Agent, or Firm*—Fitzpatrick, Cella, Harper & Scinto

[57] ABSTRACT

The present invention relates to a method for quantitative determination of 1,5-anhydroglucitol in a sample, which comprises mixing the sample and an enzyme having activity that is inhibited by 1,5-anhydroglucitol in a concentration-dependent manner, and measuring the activity of the enzyme; and a reagent for quantitative determination of 1,5-anhydroglucitol which comprises an enzyme having activity that is inhibited by 1,5-anhydroglucitol in a concentration-dependent manner, a substrate for the enzyme, and a reagent for quantitative determination of a product formed by the enzyme activity. The present invention also relates to novel trehalase having a Ki value of 0.33 mM or less for 1,5-anhydroglucitol; and a process for producing novel trehalase having the above-mentioned physicochemical properties, which comprises culturing in a medium a microorganism belonging to the genus Nocardia and capable of producing the trehalase, and recovering the trehalase from the culture.

18 Claims, 10 Drawing Sheets

METHOD FOR QUANTITATIVE DETERMINATION OF 1,5-ANHYDROGLUCITOL

BACKGROUND OF THE INVENTION

1. Field of the Invention

The present invention relates to a method for enzymatic determination of 1,5-anhydroglucitol, a reagent for use in the method, novel trehalase which is suitable for use in the method for enzymatic determination of 1,5-anhydroglucitol, and a process for producing the novel trehalase. The determination of the 1,5-anhydroglucitol concentration is useful in diagnosis of diabetes.

2. Description of Related Art

It is known that 1,5-anhydroglucitol is present in human cerebrospinal fluid and blood plasma and that the level of 1,5-anhydroglucitol changes in patients of some diseases, especially diabetes, and thus it is important as a diagnostic marker for diabetes. Previous methods for quantitatively determining 1,5-anhydroglucitol include a method using a special analytical instrument such as gas chromatography, a method using an enzyme which specifically oxidizes 1,5-anhydroglucitol (Japanese Published Unexamined Patent Application No. 79780/87), and a method which comprises converting substances such as glucose in a sample to other substances by using various enzymes, and then determining the amount of 1,5-anhydroglucitol remaining in the sample by using pyranose oxidase or L-sorbose oxidase (Japanese Published Unexamined Patent Application No. 185397/88).

Generally, instrumental analyses such as liquid chromatography and gas chromatography involve complicated pretreatment of samples, requires expensive special instruments, and is time-consuming; therefore, this method is not suitable for the analysis of a large number of samples. In the method using an enzyme which specifically acts on 1,5-anhydroglucitol, it is not easy to prepare the enzyme and to lead to an appropriate detection system. The method using pyranose oxidase has the defect that the substrate specificity of pyranose oxidase is insufficient.

SUMMARY OF THE INVENTION

The method of the present invention for the quantitative determination of 1,5-anhydroglucitol in a sample comprises (1) mixing a sample and an enzyme, wherein the activity of the enzyme is inhibited by 1,5-anhydroglucitol in a concentration-dependent manner, and (2) measuring the activity of the enzyme. The present invention also provides a reagent for quantitative determination of 1,5-anhydroglucitol composed of an enzyme, wherein the activity of the enzyme is inhibited by 1,5-anhydroglucitol in a concentration-dependent manner, a substrate for the enzyme, and a reagent for quantitative determination of a product formed by the enzyme. Preferred enzymes useful in the present invention include trehalase and trehalose phosphorylase.

The enzyme trehalase may be prepared by a process of the present invention by culturing a microorganism belonging to the genus Nocardia, having the ability to produce trehalase, and recovering the trehalase from the culture. The trehalase useful in the present invention preferably: has a Ki value of 0.33 mM or less for 1,5-anhydroglucitol; has a Km value for trehalose of 6.7 mM; has an optimum pH of 5–6 and is stable at a pH range of 5–10 when treated at 50° C. for 30 minutes; has an optimum temperature of about 45° C. and is stable up to 50° C. when treated at pH 5.0 for 30 minutes; has a molecular weight as measured by gel filtration of about 400,000; has a substrate specificity for trehalose; and is inhibited by metal chelating agents.

DETAILED DESCRIPTION OF THE INVENTION

Figure 1:
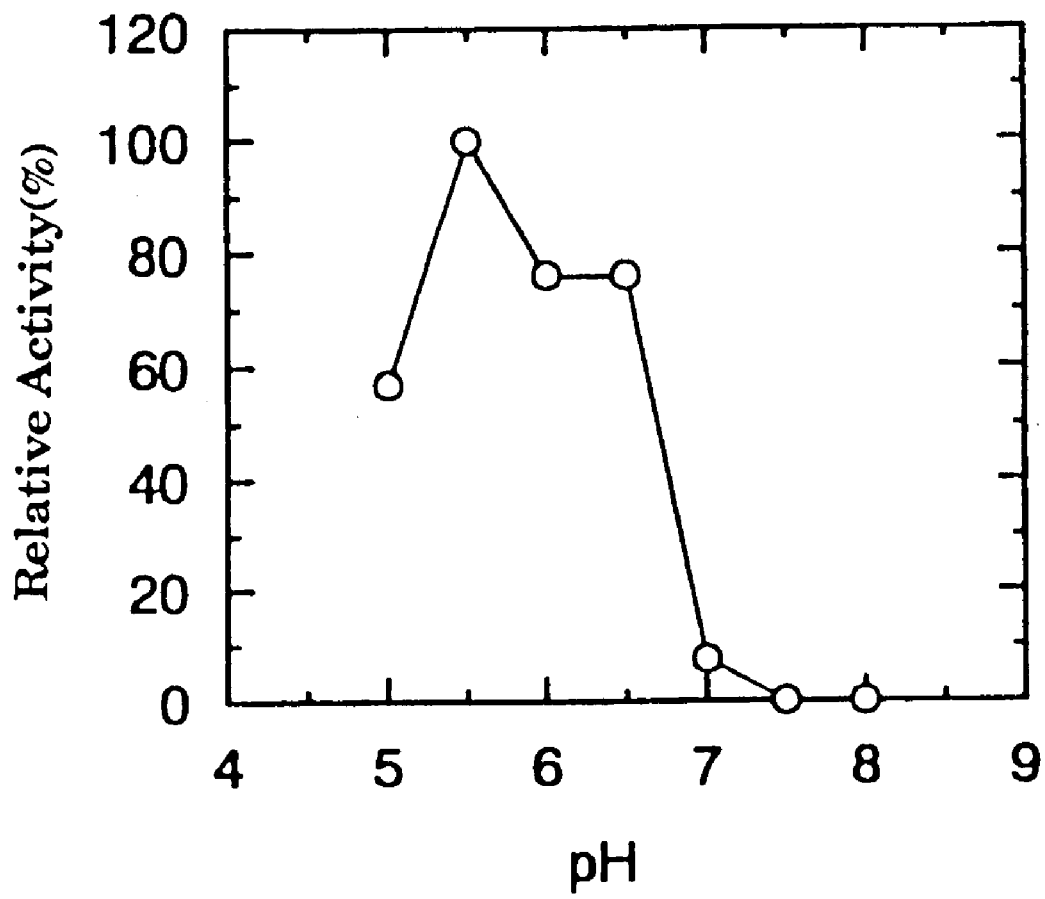
FIG. 1 shows the pH-activity curve of trehalase derived from Nocardia sp. NK-2067.

The present invention relates to the following:

a method for quantitative determination of 1,5-anhydroglucitol in a sample, which comprises mixing the sample and an enzyme having activity that is inhibited by 1,5-anhydroglucitol in a concentration-dependent manner, and measuring the activity of the enzyme;

a reagent for quantitative determination of 1,5-anhydroglucitol which comprises an enzyme having activity that is inhibited by 1,5-anhydroglucitol in a concentration-dependent manner, a substrate for the enzyme, and a reagent for quantitative determination of a product formed by the enzyme reaction;

novel trehalase having a Ki value of 0.33 mM or less for 1,5-anhydroglucitol and having the following physicochemical properties:
(1) action: it catalyzes the reaction in which 1 molecule of trehalose is hydrolyzed to form 2 molecules of D-glucose in the presence of water as shown by general formula (I):

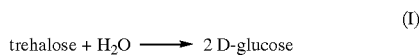

$$\text{trehalose} + H_2O \longrightarrow 2 \text{ D-glucose} \qquad (I)$$

(2) substrate specificity: it specifically acts on trehalose,
(3) substrate affinity: Km value for trehalose is 6.7 mM,
(4) optimum pH and stable pH: the optimum pH of the enzyme is 5–6, and the enzyme is stable at a pH range of 5–10, when treated at 50° C. for 30 minutes,
(5) optimum temperature and thermostability: the optimum temperature is about 45° C., and the enzyme is stable up to 50° C. when treated at pH 5.0 for 30 minutes,
(6) inhibitor: it is inhibited by metal chelating agents such as 1,10-phenanthroline, ethylenediaminetetraacetic acid (hereinafter referred to as EDTA), and 2,2'-bipyridyl, SH blocking reagents such as p-mercuribenzoic acid and iodoacetamide, hydroxylamine, nickel sulfate, etc.,
(7) molecular weight: the molecular weight of a subunit of the enzyme as measured by dodecyl sodium sulfate-polyacrylamide gel electrophoresis is about 90,000 and the molecular weight of the enzyme as measured by gel filtration method is about 400,000; and a process for producing novel trehalase having the above-mentioned physicochemical properties, which comprises culturing in a medium a microorganism belonging to the genus Nocardia and capable of producing the trehalase, and recovering the trehalase from the culture.

The present invention is applicable to assay of any samples containing 1,5-anhydroglucitol, for example, biological samples such as cerebrospinal fluid, serum, plasma and urine, and treated fluids of such samples.

As the enzyme having activity that is inhibited by 1,5-anhydroglucitol in a concentration-dependent manner, any enzyme derived from an insect, an animal, a plant, a microorganism, or the like, can be used insofar as its activity is inhibited by 1,5-anhydroglucitol in a concentration-dependent manner. Preferred examples are enzymes catalyzing trehalose as a substrate, such as trehalase and trehalose phosphorylase. These enzymes can be obtained as commercial products, or may be prepared by culturing a microorganism.

Microorganisms which produce trehalase include microorganisms belonging to the genus Streptomyces, Nocardia, or Rhodococcus.

Examples of the microorganisms belonging to the genus Streptomyces are *Streptomyces aureofaciens* ATCC 10762 and *Streptomyces chromofuscus* ATCC 23896. An example of the microorganisms belonging to the genus Nocardia is *Nocardia transvalensis* ATCC 6865. Examples of the microorganisms belonging to the genus Rhodococcus are *Rhodococcus globerulus* ATCC 14898, *Rhodococcus globerulus* ATCC 15076 and *Rhodococcus rhodochrous* ATCC 17895.

Microorganisms which produce trehalose phosphorylase include microorganisms belonging to the genus Catellatospora or Kineosporia.

An example of the microorganisms belonging to the genus Catellatospora is *Catellatospora ferruginea* FERM BP-4329. An example of the microorganisms belonging to the genus Kineosporia is *Kineosporia aurantiaca* ATCC 29727.

The mycological properties of the species to which the above microorganisms belong are described in the following literature.

*Streptomyces aureofaciens:*
  Bergey's Manual of Systematic Bacteriology,
  Vol. 4, p. 2478 (1989)
*Streptomyces chromofuscus:*
  Bergey's Manual of Systematic Bacteriology,
  Vol. 4, p. 2472 (1989)
*Nocardia transvalensis:*
  Bergey's Manual of Systematic Bacteriology,
  Vol. 2, p. 1469 (1986) and Vol. 4, p. 2359 (1989)
*Rhodococcus globerulus:*
  Bergey's Manual of Systematic Bacteriology,
  Vol. 2, p. 1479 (1986) and Vol. 4, p. 2369 (1989)
*Rhodococcus rhodochrous:*
  Bergey's Manual of Systematic Bacteriology,
  Vol. 4, p. 2365–2367 (1989)
*Catellatospora ferruginea:*
  Int. J. Syst. Bacteriol., 36, 512–517 (1986)
*Kineosporia aurantiaca:*
  Bergey's Manual of Systematic Bacteriology,
  Vol. 4, p. 2504–2506 (1989)

The method for culturing the above microorganisms and the method for purifying the enzymes produced by them are described below.

For the culturing of the microorganisms which produce trehalase, e.g., microorganisms belonging to the genus Streptomyces, Nocardia or Rhodococcus and the microorganisms which produce trehalose phosphorylase, e.g., microorganisms belonging to the genus Catellatospora or Kineosporia, conventional methods for culturing actinomycetes, bacteria, etc. are employed.

As the medium, either a natural medium or a synthetic medium may be used insofar as it contains carbon sources, nitrogen sources, inorganic salts, etc.

As the carbon sources, carbohydrates, sugar alcohols, organic acids, etc. can be used. Examples of the carbohydrates are glucose, sucrose, maltose, trehalose, starch, and molasses. Examples of the sugar alcohols are glycerol, sorbitol, and mannitol. Examples of the organic acids are acetic acid, lactic acid, pyruvic acid, and citric acid.

As the nitrogen sources, inorganic or organic ammonium salts, nitrogen-containing organic substances, etc. can be used. Examples of the inorganic or organic ammonium salts are ammonia, ammonium chloride, ammonium carbonate, ammonium phosphate, and ammonium acetate. Examples of the nitrogen-containing organic substances are urea, amino acids, peptone, NZ-amine, meat extract, corn steep liquor, casein hydrolyzate, and yeast extract.

As the inorganic salts, potassium dihydrogenphosphate, dipotassium hydrogenphosphate, potassium chloride, sodium chloride, magnesium sulfate, ferrous sulfate, etc. can be used.

As the method of culturing, liquid culture, especially submerged stirring culture, is preferably employed. Culturing is carried out at pH 6.0 to 8.0 and at a temperature of 25 to 37° C. for 1 to 7 days by static culture or with aeration and stirring.

By culturing the microorganism in the above manner, trehalase or trehalose phosphorylase is formed and accumulated in the culture, mainly in microbial cells. Recovery of trehalase or trehalose phosphorylase from the culture can be carried out, for example, in the following manner.

After the completion of culturing, the microbial cells are collected from the culture by centrifugation or filtration, and then disrupted by ultrasonic disruption or the like to obtain a crude enzyme extract. The crude enzyme extract is treated according to the methods usually used for purification of enzymes such as salting-out, precipitation with an organic solvent, dialysis, ion-exchange column chromatography, gel filtration, and lyophilization, whereby purified trehalase or purified trehalose phosphorylase can be obtained.

The physicochemical properties of the novel trehalase of the present invention are as follows.

(1) Action

The enzyme of the present invention catalyzes the reaction in which 1 molecule of trehalose is hydrolyzed to form 2 molecules of D-glucose in the presence of water as shown by general formula (I).

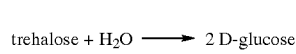

(I)

(2) Substrate specificity and inhibition specificity

The activity of the enzyme on various substrates was measured at a substrate concentration of 1.75 mM in 100 mM phosphate buffer (pH 5.5). The results are shown in Table 1 as relative activities, the activity on trehalose being defined as 100.

TABLE 1

| Sugar | Relative activity (%) |
| --- | --- |
| Trehalose | 100 |
| Trehalosamine | 0.5 |
| Kojibiose | 0 |
| Nigerose | 0 |
| Maltose | 0 |
| Lactose | 0 |
| Sucrose | 0 |

As apparent from Table 1, the enzyme specifically acts on trehalose. The enzyme was also examined for inhibition specificity to various sugars at 1.75 mM using trehalose as a substrate. The results are shown in Table 2.

TABLE 2

| Sugar | Inhibition (%) |
| --- | --- |
| 1,5-Anhydroglucitol | 80.7 |
| Kojibiose | 0 |
| Nigerose | 0 |
| Maltose | 0 |
| Lactose | 0 |
| Sucrose | 0 |

(3) Substrate affinity

The Km value of the enzyme for trehalose at pH 5.5 as determined by Lineweaver-Burk plot [J. Am. Chem. Soc., 56, 658 (1934)] is 6.7 mM.

(4) Inhibitor affinity

The Ki value of the enzyme for 1,5-anhydroglucitol at pH 5.5 as determined by Lineweaver-Burk plot is 0.33 mM.

(5) Optimum pH

The activity of the enzyme was measured using phosphate buffers of pH 5.0–8.0 to determine the optimum pH, and the pH-activity curve shown in FIG. 1 was obtained. The optimum pH for the enzyme is 5–6.

(6) pH Stability

Figure 2:
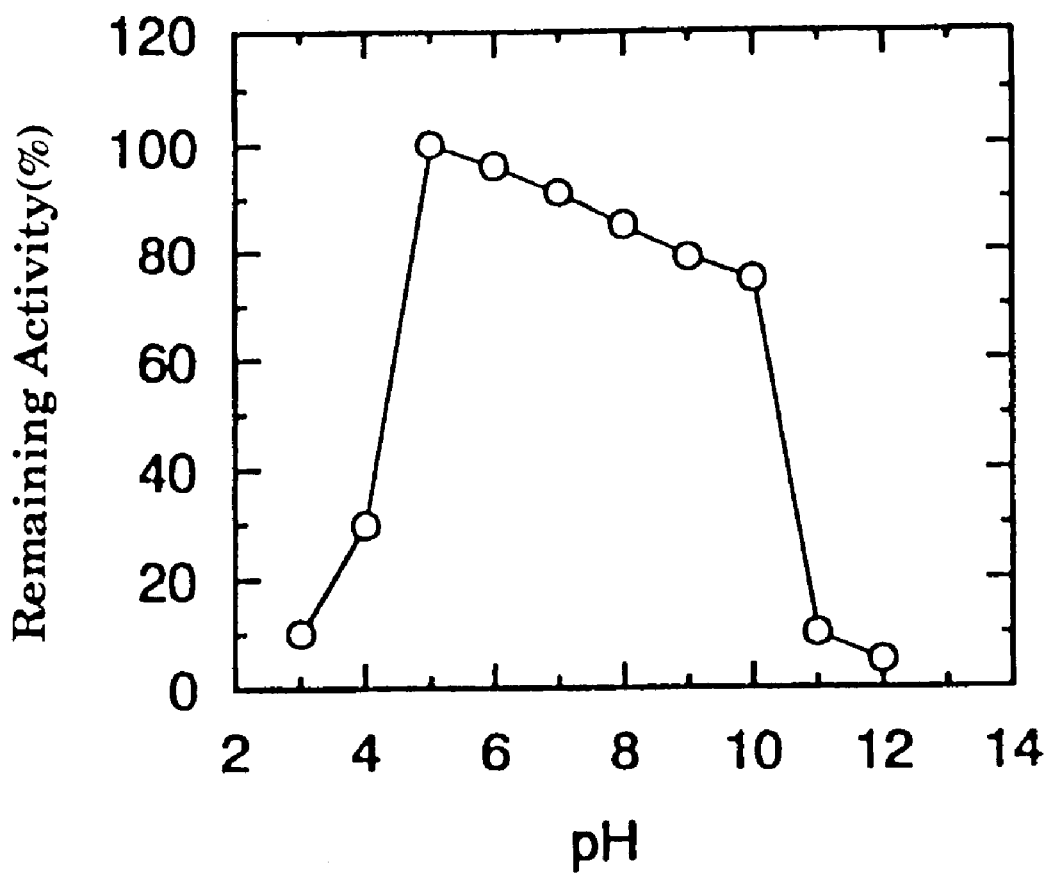
FIG. 2 shows the pH-stability curve of trehalase derived from Nocardia sp. NK-2067.

After treatment in Universal buffer (Johnson-Lindsay buffer, Basic Methods for Biochemistry, Vol. 6, Maruzen) of pH 2.6–12.0 at 50° C. for 30 minutes, the residual enzyme activity was measured. As shown in FIG. 2, the enzyme is stable at a pH range of 5–10.

(7) Thermostability

Figure 3:
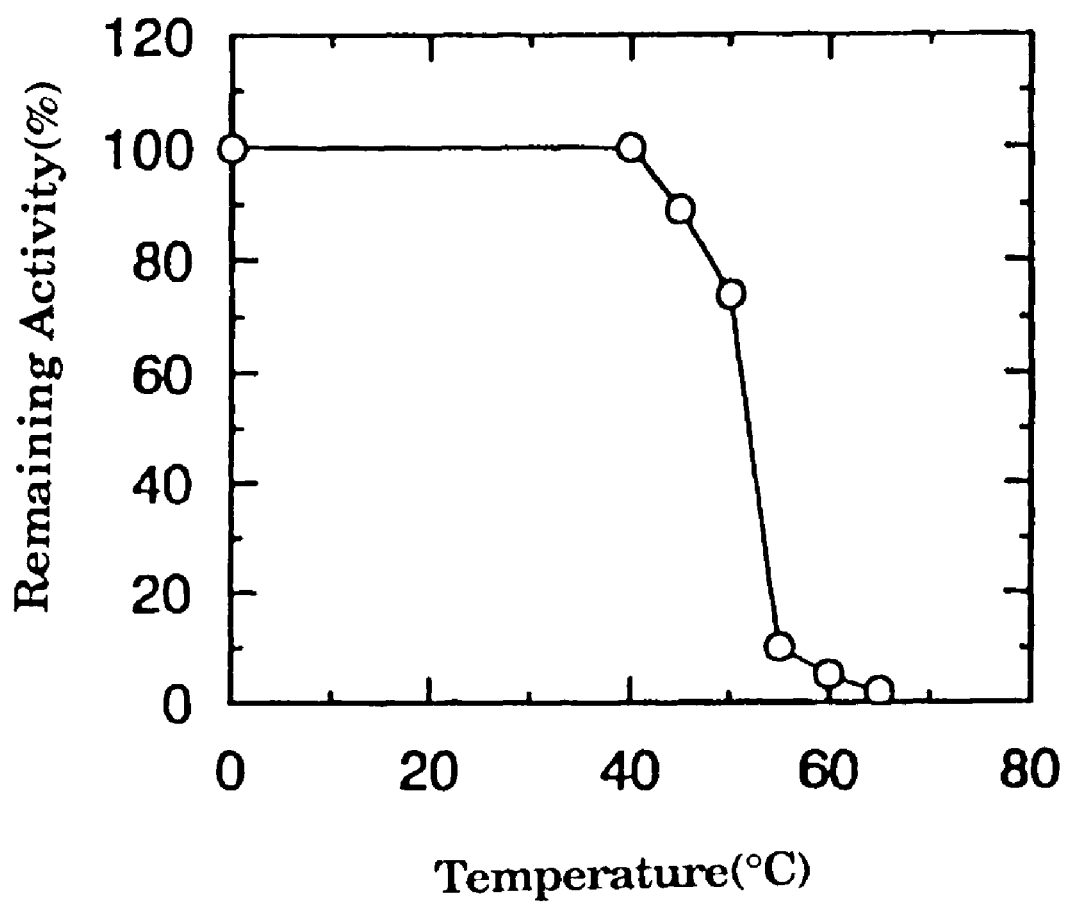
FIG. 3 shows the thermostability curve of trehalase derived from Nocardia sp. NK-2067.

The thermostability of the enzyme was investigated by keeping the enzyme at various temperatures for 30 minutes in a phosphate buffer of pH 5.0 and measuring the residual activity. As shown in FIG. 3, the enzyme is stable up to 50° C.

(8) Optimum temperature

Figure 4:
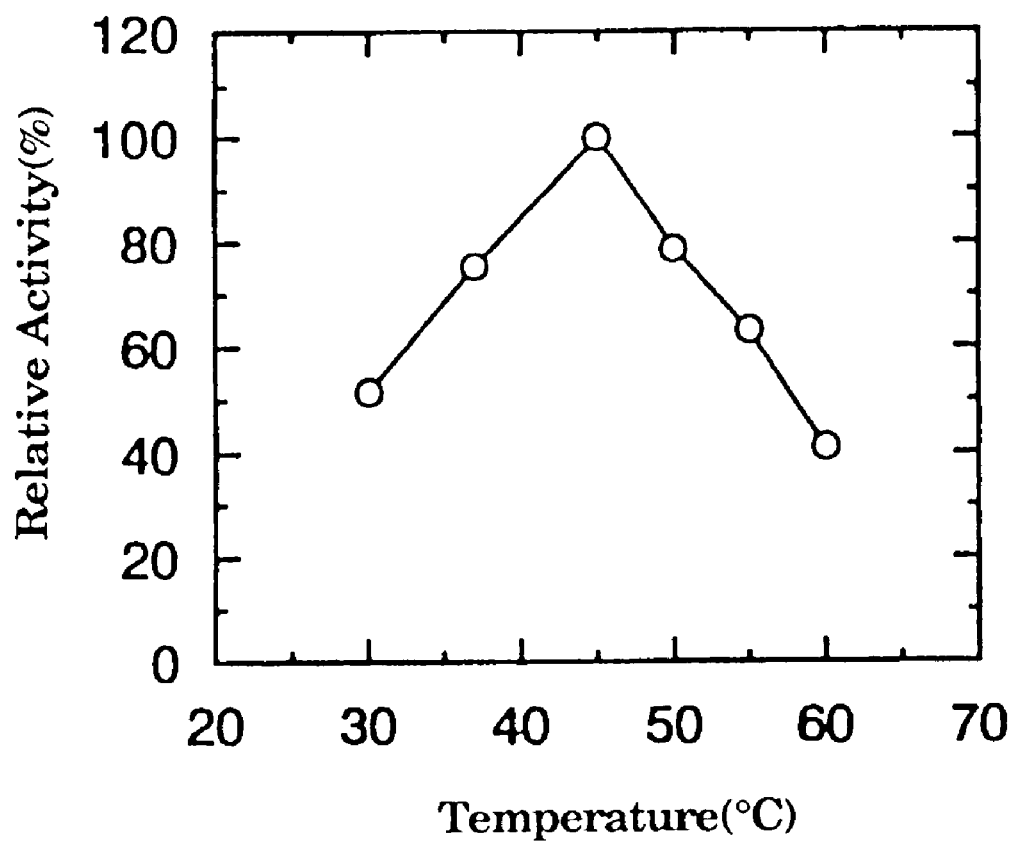
FIG. 4 shows the temperature-activity curve of trehalase derived from Nocardia sp. NK-2067.

The optimum temperature for the enzyme was determined using a phosphate buffer of pH 5.5. As shown in FIG. 4, the optimum temperature is about 45° C.

(9) Effect of inhibitors and metal ions

The effect of various metal chelating agents, enzyme inhibitors and metal ions on the enzyme was investigated at a concentration of 1 mM. The results are shown in Table 3.

TABLE 3

| Compound | Inhibition (%) |
| --- | --- |
| Diethyldithiocarbamic acid | 51.0 |
| 2,2'-Bipyridyl | 60.0 |
| EDTA | 67.6 |
| 1,10-Phenanthroline | 88.5 |
| p-Mercuribenzoic acid | 94.7 |
| N-Ethylmaleimide | 21.9 |
| Iodoacetamide | 83.6 |
| N-Bromosuccinimide | 23.4 |
| Hydroxylamine | 81.2 |
| Sodium azide | 22.8 |
| $CoCl_2$ | 20.4 |
| $NiSO_4$ | 62.1 |
| $ZnSO_4$ | 53.4 |
| $BaCl_2$ | 40.7 |

The enzyme is inhibited by metal chelating agents such as 1,10-phenanthroline, ethylenediaminetetraacetic acid and 2,2'-bipyridyl, SH blocking reagents such as p-mercuribenzoic acid and iodoacetamide, hydroxylamine, nickel sulfate, etc.

(10) Molecular weight

The molecular weight of a subunit of the enzyme as measured by dodecyl sodium sulfate-polyacrylamide gel electrophoresis is about 90,000, and the molecular weight of the enzyme as measured by gel filtration method using high performance liquid chromatography is about 400,000.

(11) Homogeneity

The enzyme was separated as a single band by dodecyl sodium sulfate-polyacrylamide gel electrophoresis. That is, a single band of a protein was observed by electrophoresis in Tris-glycine buffer (pH 8.3) for 60 minutes, followed by staining with Coomassie staining solution.

(12) Method for the measurement of enzyme activity

The enzyme activity is measured in the following manner.

1) Reagent (i) Substrate solution

Trehalose is dissolved in 100 mM phosphate buffer (pH 5.5) to give a concentration of 12.5 mM.

(ii) Color-producing reagent

Glucose oxidase (Toyobo Co., Ltd., Grade II), peroxidase (Toyobo Co., Ltd., Grade III), 4-aminoantipyrine and phenol are dissolved in water to give final concentrations of 0.04 mg/ml, 0.04 mg/ml, 1.2 mM and 21 mM, respectively.

2) Procedure

To 1 ml of the substrate solution is added 0.02 ml of an enzyme solution, and reaction is carried out at 37° C. for 30 minutes. The reaction is stopped by heating at 100° C. for 3 minutes. To the reaction mixture is added 1 ml of the color-producing reagent, and reaction is carried out at 37° C. for 20 minutes, followed by measurement of the absorbance at 500 nm. A control solution is prepared by using water instead of the enzyme solution in the above procedure.

3) Calculation of the activity

The trehalase activity is expressed by unit, one unit being defined as that amount of the enzyme which will hydrolyze 1 $\mu$mol of trehalose at 37° C. in one minute. The activity per milliliter of enzyme solution (U/ml) can be calculated from the net difference in absorbance (enzyme solution−control solution) according to the following equation.

$$\text{Activity (U/ml)} = \frac{2.02 \text{ml} \times \text{Difference in absorbance}}{5.33 \times 0.02 \text{ml} \times 30 \text{min.} \times 2}$$

The process for producing the novel trehalase of the present invention is described below. In the process, a microorganism belonging to the genus Nocardia and capable of producing the novel trehalase described above is used. A typical example of a suitable strain is Nocardia sp. NK-2067, which is a strain isolated from soil by the present inventors. The mycological properties of the strain are shown below. The experiments for investigating the mycological properties were carried out mainly according to the descriptions in Takeji Hasegawa: Classification and Identification of Microorganisms, University of Tokyo Press (1975). Classification and identification of the strain were made referring to Bergey's Manual of Systematic Bacteriology, Vol. 1–4 (1986–1989), etc.

The present inventors have found that the actinomycete NK-2067 belonging to the genus Nocardia which was newly isolated from soil is capable of producing trehalase which is highly sensitive to 1,5-anhydroglucitol.

The morphological, cultural and physiological characteristics of the above actinomycete NK-2067 are described below.

1. Morphological characteristics
1) Hyphae
   Formation of aerial hyphae: Simple branching
   Fragmentation of aerial hyphae: Observed
   Fragmentation of substrate hyphae: Observed
2) Spores
   Formation and location of spores:
      Formed on the aerial hyphae
   Formation and location of sporangia: Not observed
   Number of spores in chain formed at the end of the sporophore: 10 or more
   Characteristics of spores:
      Surface structure; Smooth
      Form and size;
      Form and size;
         Rod, ca. 0.7~1.0 $\mu$m×0.7~2.0 $\mu$m
      Motility of spores and existence of flagella; Not observed
3) Others
   Chlamydospores; Not observed
   Synnemata; Not observed
   Pseudosporangia; Not observed
   Branching mode of hyphae; Simple branching
2. Cultural characteristics The NK-2067 strain shows moderate or good growth on synthetic media and natural media which are generally used. The color of the substrate hyphae is white to pale pink. Formation of soluble brown pigment may be observed on some of the culture media.

The cultural characteristics such as growth and color of NK-2067 strain on various media observed after culturing at 28° C. for 14 days are shown below. The color names were given according to the Color Harmony Manual [Container Corporation of America, 4th edition (1958)].

1) Sucrose-nitrate agar medium
   Growth; Poor
   Color of substrate hyphae; White (a)
   Formation and color of aerial hyphae; Not formed
   Soluble pigment; None
2) Glucose-asparagine agar medium
   Growth; Good
   Color of substrate hyphae;
      Flesh pink (4ca)-dusty peach (5ec)
   Formation and color of aerial hyphae;
      Moderate, white (a)
   Soluble pigment; None
3) Glycerol-asparagine agar medium
   Growth; Good
   Color of substrate hyphae;
      Flesh pink (5ca)-light rose beige (4ec)
   Formation and color of aerial hyphae; Poor, white (a)
   Soluble pigment; None
4) Starch-inorganic salts agar medium
   Growth; Poor
   Color of substrate hyphae; Oatmeal (2ec)
   Formation and color of aerial hyphae; Not formed
   Soluble pigment; None
5) Tyrosine agar medium
   Growth; Good
   Color of substrate hyphae;
      Nude tan (4gc)-cork tan (4ie)
   Formation and color of aerial hyphae; Poor, white (a)
   Soluble pigment; Formed (reddish brown)
6) Nutrient agar medium
   Growth; Good
   Color of substrate hyphae; Light mustard tan (2ie)
   Formation and color of aerial hyphae; Not formed
   Soluble pigment; None
7) Yeast-malt agar medium
   Growth; Good
   Color of substrate hyphae; Cinnamon (3le)
   Formation and color of aerial hyphae; Not formed
   Soluble pigment; Formed only a little (ocher)
8) Oatmeal agar medium
   Growth; Poor
   Color of substrate hyphae; Oatmeal (2ec)
   Formation and color of aerial hyphae; Not formed
   Soluble pigment; None
3. Physiological characteristics The physiological characteristics of NK-2067 strain are shown below. The growth temperature range was determined after 14 days of culturing and the other results were obtained after 2 to 3 weeks of culturing at 28° C.

1) Growth temperature range; 6–36° C.
2) Liquefaction of gelatin; Positive
3) Hydrolysis of starch; Negative
4) Coagulation and peptonization of skim milk powder;
   Negative 5) Production of melanin-like pigment
   (i) Peptone-yeast-iron agar medium; Positive
   (ii) Tyrosine agar medium; Positive
6) Assimilability of carbon sources As the basic medium, Pridham Gottlieb agar medium was used. In the following, + indicates that the strain utilized the carbon source, and − indicates that the strain did not utilize the carbon source.

| | |
|---|---|
| L-Arabinose; | − |
| D-Xylose; | − |
| D-Glucose; | + |
| Sucrose; | + |
| Raffinose; | − |
| D-Fructose; | + |
| Rhamnose; | − |
| Inositol; | + |
| D-Mannitol; | − |

7) Degradability

As the basic medium, nutrient agar medium was used. In the following, + indicates that the strain degraded the substance, and − indicates that the strain did not degrade the substance.

| | |
|---|---|
| Tyrosine; | − |
| Adenine; | − |
| Xanthine; | + |
| Hypoxanthine; | + |
| Urea; | + |

8) Acid producibility

As the basic medium, peptone liquid medium was used (Bromothymol Blue was used as an indicator). In the following, + indicates that the strain produced an acid, and − indicates that the strain did not produce an acid.

| | |
|---|---|
| Glucose; | + |
| Galactose; | − |
| Inositol; | − |
| Maltose; | − |
| Mannose; | − |
| Rhamnose; | − |
| Sorbitol; | − |
| Arabinose; | − |
| Adonitol; | − |

9) NaCl Resistance

As the basic medium, nutrient agar medium was used. In the following, + indicates that the strain grew, and − indicates that the strain did not grow.

| | |
|---|---|
| 0% NaCl; | + |
| 1% NaCl; | + |
| 2% NaCl; | + |
| 4% NaCl; | − |
| 6% NaCl; | − |
| 10% NaCl; | − |

4. Chemotaxonomic characteristics
1) Optical isomer of diaminopimelic acid in the strain; meso-form
2) Major quinone component of cellular lipid;
   MK (menaquinone)-8 (II, III-H4, ω-cycle)
3) Mycolic acid in cellular lipid; Contained
4) Major sugar component of whole cell; Arabinose and galactose The strain was confirmed to belong to the genus Nocardia among actinomycetes by its morphological characteristics that fragmentation of substrate hyphae was observed, and spore chains were formed on the aerial hyphae; and its chemotaxonomic characteristics that meso-diaminopimelic acid, arabinose and galactose were detected in the cell wall, glycine was not detected, the major quinone component was tetrahydrogenated menaquinone-8, omega cycle [MK-8 (II, III-H4, ω-cycle)], and mycolic acid was contained.

This strain was named Nocardia sp. NK-2067 and was deposited at the National Institute of Bioscience and Human-Technology, Agency of Industrial Science and Technology, Ministry of International Trade and Industry (1-3, Higashi 1-chome, Tsukuba-shi, Ibaraki 305 Japan) on Jan. 11, 1996 with accession number FERM BP-5359.

For the production of the above-described novel trehalase using a microorganism of the genus Nocardia, methods similar to the previously described methods for culturing microorganisms and purifying the formed enzyme are employed.

The method for quantitative determination of 1,5-anhydroglucitol in a sample which comprises mixing the sample and an enzyme having activity that is inhibited by 1,5-anhydroglucitol in a concentration-dependent manner, and measuring the activity of the enzyme is described below.

The concentration of 1,5-anhydroglucitol in a sample can be determined from the activity of an enzyme having activity that is inhibited by 1,5-anhydroglucitol in a concentration-dependent manner as determined in the presence of the sample, by using a calibration curve prepared in advance from the activity of the enzyme determined in the presence of 1,5-anhydroglucitol at known concentrations and the 1,5-anhydroglucitol concentration.

Alternatively, the difference between the activity of the enzyme in the absence of (A) and that in the presence of 1,5-anhydroglucitol (B), or the inhibition rate calculated according to the following equation can be used for the calibration curve instead of the activity of the enzyme determined in the presence of 1,5-anhydroglucitol.

Inhibition rate (%)=[(A−B)/A×100]

A: the enzyme activity in the absence of 1,5-anhydroglucitol

B: the enzyme activity in the presence of 1,5-anhydroglucitol

The activity of the enzyme having activity that is inhibited by 1,5-anhydroglucitol in a concentration-dependent manner can be measured by ordinary methods for measuring enzyme activity. The enzyme reaction is carried out at 10–50° C. for 1–60 minutes, preferably 1–20 minutes, more preferably at 25–40° C. for 5–15 minutes, in a reaction mixture prepared by adding the enzyme, a substrate for the enzyme and if necessary, an enzyme activity moderator to an aqueous medium. Measurement of the enzyme activity is carried out by measuring the concentration of a product formed or the substrate remaining as a result of the enzyme reaction under certain conditions; or by converting the product formed or the substrate remaining into other substances and then measuring the concentration thereof.

As the aqueous medium, water-containing liquids such as buffers and physiological saline can be used. Buffers are preferably used.

Examples of the buffers are lactate buffer, citrate buffer, acetate buffer, succinate buffer, phthalate buffer, phosphate buffer, triethanolamine buffer, diethanolamine buffer, lysine buffer, barbital buffer, tris(hydroxymethyl)aminomethane buffer, imidazole buffer, malate buffer, oxalate buffer, glycine buffer, borate buffer, carbonate buffer, and Good's buffer.

Examples of the enzyme activity moderators are metal chelating agents such as EDTA and 1,10-phenanthroline, sugar alcohols such as mannitol and glycerol, metal ions such as zinc and copper, and SH blocking reagents such as iodoacetic acid and iodoacetamide.

The procedure for the determination of 1,5-anhydroglucitol in which trehalase is used as the enzyme having activity that is inhibited by 1,5-anhydroglucitol is described below.

Trehalase catalyzes the reaction represented by formula (I), in which 2 molecules of D-glucose is formed from 1 molecule of trehalose and 1 molecule of water.

trehalose+H$_2$O→2 D-glucose (I)

The enzyme reaction is carried out at 10–50° C. for 1–20 minutes, preferably at 25–40° C. for 5–15 minutes, in a reaction mixture prepared by adding trehalose, trehalase, and if necessary, the enzyme activity moderator mentioned above to the aqueous medium mentioned above.

The enzyme activity can be measured by chemical or biochemical methods used for the determination of D-glucose. The amount of D-glucose increased can be measured by direct methods wherein the increase in reducing power, etc. is chemically measured, or by methods wherein D-glucose is converted into another substance for measurement. Particularly preferred are methods utilizing enzymes which have high specificity to D-glucose and which are applicable to automatic biochemical analyzers for wide use.

Examples of such methods are: 1) a method wherein D-glucose is oxidized by using glucose oxidase, and hydrogen peroxide formed by the reaction is determined colorimetrically; 2) a method wherein D-glucose is oxidized by using pyranose oxidase, and hydrogen peroxide formed by the reaction is determined colorimetrically; 3) a method wherein D-glucose is dehydrogenated by using glucose dehydrogenase in the presence of a coenzyme nicotinamide adenine dinucleotide (hereinafter referred to as NAD) or nicotinamide adenine dinucleotide phosphate (hereinafter referred to as NADP), and the absorbance of NADH or NADPH, both of which are reduced form of the coenzyme formed by the reaction, is measured with a spectrophotometer; and 4) a method wherein D-glucose is phosphorylated by using hexokinase or glucokinase in the presence of adenosine triphosphate, D-glucose-6-phosphate formed is dehydrogenated by using glucose-6-phosphate dehydrogenase in the presence of a coenzyme NADP, and the absorbance of NADPH formed by the reaction is measured with a spectrophotometer.

As described above, the determination of D-glucose can be carried out by enzymatically converting D-glucose into an intermediate which can be readily determined, such as hydrogen peroxide or a coenzyme (e.g. NADH and NADPH mentioned above), and determining the amount of the intermediate. Hydrogen peroxide can be determined by methods such as colorimetry, fluorometry, chemiluminescence analysis and electrode method, and the coenzymes NADH and NADPH can be determined, for example, by colorimetry.

The colorimetry can be carried out by reaction of hydrogen peroxide with a color reagent in the presence of an enzyme such as peroxidase to develop color, followed by measurement with a spectrophotometer. As the color reagent, Trinder's reagents and leuco reagents can be used.

Examples of the Trinder's reagents are combinations of 4-aminoantipyrine and phenol compounds such as phenol and 3-hydroxy-2,4,6-triiodobenzoic acid, and combinations of 4-aminoantipyrine and aniline compounds such as N-ethyl-N-(2-hydroxy-3-sulfopropyl)-m-toluidine, N-ethyl-N-(2-hydroxy-3-sulfopropyl)-3,5-dimethoxyaniline, sodium N-(2-hydroxy-3-sulfopropyl)-3,5-dimethoxyaniline, and N-ethyl-N-(3-methylphenyl)-N'-succinylethylenediamine (hereinafter referred to as EMSE).

Examples of the leuco reagents are 10-N-carboxymethylcarbamoyl-3,7-bis(dimethylamino)-10H-phenothiadine, 10-N-methylcarbamoyl-3,7-bis(dimethylamino)-10H-phenothiadine, sodium N-(carboxymethylaminocarbonyl)-4,4'-bis(dimethylamino) diphenylamine, 4,4'-bis(dimethylamino)diphenylamine, and bis[3-bis(4-chlorophenyl)methyl-4-dimethylaminophenyl] amine.

The fluorometry can be carried out by reaction of hydrogen peroxide with a fluorescence reagent in the presence of an enzyme such as peroxidase to form a fluorescent substance, followed by measurement with a fluorophotometer. As the fluorescence reagent, p-hydroxyphenylacetic acid, p-hydroxyphenylpropionic acid, coumarin, etc. can be used.

The chemiluminescence analysis can be carried out by reaction of hydrogen peroxide with a luminescence reagent in the presence of an enzyme such as peroxidase to form photon, followed by measurement with a luminometer. As the luminescence reagent, luminol, isoluminol, lucigenin, acridinium ester, etc. can be used.

The coenzymes such as NADH and NADPH can be determined directly by measuring the absorbance. Alternatively, they can be determined after conversion into other substances. For example, NADPH can be determined by reacting NADPH with a tetrazolium salt and measuring the amount of a formazan pigment formed by the reaction by using a spectrophotometer.

The procedure for the measurement of enzyme activity according to the method of 1) above is described below. The enzyme activity of trehalase is measured by carrying out the reaction shown by formula (II) to form a quinoneimine pigment and measuring the concentration of the pigment with a spectrophotometer.

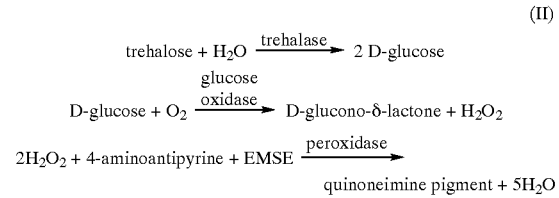

The reaction mixture for use in the assay according to this method is prepared by adding trehalase, glucose oxidase, peroxidase, trehalose, 4-aminoantipyrine, EMSE, etc. to a buffer such as phosphate buffer. The pH of the phosphate buffer is preferably 5.0–8.0, more preferably 6.0–7.0, and the concentration thereof is preferably 10–500 mM, more preferably 50–250 mM.

The concentrations of the substances added to the buffer are as follows: trehalase, preferably 0.001–10 U/ml, more preferably 0.01–1 U/ml; glucose oxidase, preferably 1–100 U/ml, more preferably 10–50 U/ml; peroxidase, preferably 1–50 U/ml, more preferably 5–20 U/ml; trehalose, preferably 1–100 mM, more preferably 10–50 mM; 4-aminoantipyrine, preferably 0.5–50 mM, more preferably 1–10 mM; EMSE, preferably 0.5–50 mM, more preferably 1–10 mM.

To the above-described reaction mixture is added a sample containing 1,5-anhydroglucitol, and reaction is carried out at 10–50° C. for 1–20 minutes, preferably at 25–40° C. for 5–15 minutes. The enzyme activity can be determined from the concentration of the quinoneimine pigment formed by the reaction which is determined by measuring the absorbance at 550 nm.

In cases where D-glucose is present in a sample, it is preferred to eliminate D-glucose in the sample in advance in the following manner. Examples of the samples containing D-glucose are blood, serum, and plasma.

The elimination of D-glucose in samples can be effected by physical methods wherein D-glucose is adsorbed and removed using a column, etc., and chemical or biochemical methods wherein D-glucose is converted into another substance. Biochemical conversion methods using enzymes are preferably employed for the assay using automatic biochemical analyzers.

D-Glucose can be converted into another substance by the above-described conversion methods used in the determination of D-glucose. Examples of such methods are: 1) a method wherein D-glucose is converted into D-glucono-δ-lactone by using glucose oxidase; 2) a method wherein D-glucose is converted into 2-dehydro-D-glucose by using pyranose oxidase; 3) a method wherein D-glucose is converted into D-glucono-δ-lactone by using glucose dehydrogenase; and 4) a method wherein D-glucose is converted into D-glucono-δ-lactone-6-phosphate by using hexokinase or glucokinase, and glucose-6-phosphate dehydrogenase.

The assay of samples containing D-glucose can be carried out in the following manner. For example, D-glucose in a sample is converted into another substance by the method of 1) or 2) above, hydrogen peroxide formed is eliminated by the method described in Japanese Published Unexamined Patent Application No. 83287/82, reaction using the action of trehalase is carried out, and the amount of D-glucose formed by the reaction is determined. Alternatively, D-glucose in a sample is converted into another substance by the method of 3) or 4) above, and NADH or NADPH formed is converted into another substance by using NADH oxidase, NADPH oxidase, or the like. In the case where the method of 4) is employed, adenosine triphosphate remaining in the reaction mixture is converted into another substance by using diaphorase, adenosine triphosphatase, or the like. Then, reaction using the action of trehalase is carried out, and the amount of D-glucose formed by the reaction is determined, for example, by the method of 1) or 2) above.

A representative procedure for the determination of 1,5-anhydroglucitol involving the elimination of D-glucose in a sample comprises the steps of: converting D-glucose into D-glucono-δ-lactone and hydrogen peroxide by using glucose oxidase; eliminating the formed hydrogen peroxide by reaction with a hydrogen peroxide-eliminating compound such as EMSE in the presence of peroxidase; and measuring the trehalase activity according to the above method shown by formula (II).

In this procedure, a reaction mixture prepared by adding glucose oxidase, peroxidase, EMSE, etc. to a buffer such as phosphate buffer is subjected to reaction with a sample at 10–50° C. for 1–20 minutes, preferably at 25–40° C. for 5–15 minutes, to eliminate D-glucose in the sample. To the reaction mixture is added a reagent containing trehalose, trehalase, 4-aminoantipyrine, etc., and the trehalase activity is measured by the method described above. The concentrations of the components of the reagent are the same as above.

Another representative procedure comprises the steps of: converting D-glucose into D-glucose-6-phosphate by using glucokinase in the presence of adenosine triphosphate; converting D-glucose-6-phosphate and NADP into D-glucono-δ-lactone-6-phosphate and NADPH by using glucose-6-phosphate dehydrogenase; decomposing adenosine triphosphate by using adenosine triphosphatase; and measuring the trehalase activity according to the above method shown by formula (II).

In this procedure, a reaction mixture prepared by adding glucokinase, ATP, glucose-6-phosphate dehydrogenase, and NADP to a buffer such as phosphate buffer is subjected to reaction with a sample at 10–50° C. for 1–20 minutes, preferably at 25–40° C. for 5–15 minutes, to eliminate D-glucose in the sample. After adenosine triphosphate remaining in the reaction mixture is decomposed by addition of adenosine triphosphatase, a reagent containing trehalose, trehalase, peroxidase, 4-aminoantipyrine, EMSE, etc. is added to the reaction mixture, and the trehalase activity is measured by the method described above. The concentrations of the components of the reagent are the same as above. The concentrations of the substances contained in the reaction mixture are as follows: glucokinase, preferably 0.1–100 U/ml, more preferably 1–10 U/ml; glucose-6-phosphate dehydrogenase, preferably 0.1–100 U/ml, more preferably 1–10 U/ml; adenosine triphosphatase, preferably 0.1–100 U/ml, more preferably 1–10 U/ml; NADP, preferably 1–100 mM, more preferably 10–50 mM; adenosine triphosphate, preferably 1–100 mM, more preferably 10–50 mM. The other compounds and enzymes are used at the same concentrations as above.

Next, a description about trehalose phosphorylase is given below. Trehalose phosphorylase catalyzes reversibly the reaction shown by formula (III).

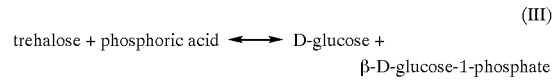

(III)

The enzyme activity of trehalose phosphorylase can be measured by direct methods wherein the change in concentration of D-glucose, β-D-glucose-1-phosphate, trehalose, or phosphoric acid is measured by known methods, or by methods wherein these substances are converted into other substances for measurement. For instance, the enzyme activity in the reaction of formula (III) in the right direction can be measured by carrying out the reaction of formula (IV) and optically measuring the concentration of NADPH formed by the reaction.

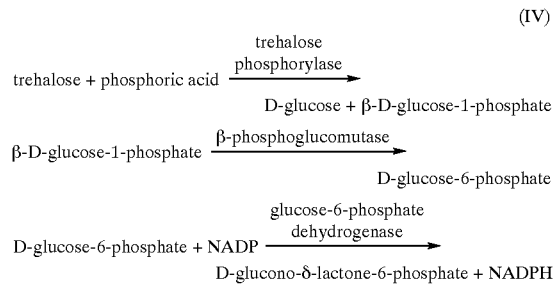

(IV)

The reaction mixture for the measurement of this enzyme activity is prepared by adding trehalose phosphorylase, β-phosphoglucomutase, glucose-6-phosphate dehydrogenase, trehalose, NADP, etc. to a buffer such as phosphate buffer. The pH of the phosphate buffer is preferably 5.0–8.0, more preferably 6.0–7.0, and the concentration thereof is preferably 10–500 mM, more preferably 50–250 mM.

The concentrations of the substances added to the buffer are as follows: trehalose phosphorylase, preferably 0.001–10 U/ml, more preferably 0.01–1 U/ml; β-phosphoglucomutase, preferably 0.1–50 U/ml, more preferably 1–10 U/ml; glucose-6-phosphate dehydrogenase, preferably 0.1–50 U/ml, more preferably 1–10 U/ml; trehalose, preferably 1–100 mM, more preferably 10–50 mM; NADP, preferably 1–50 mM, more preferably 5–20 mM.

To the above-described reaction mixture is added a sample containing 1,5-anhydroglucitol, and reaction is carried out at 10–50° C. for 1–20 minutes, preferably at 25–40° C. for 5–15 minutes. The enzyme activity can be determined from the concentration of NADPH formed by the reaction which is determined by measuring the absorbance at 340 nm.

The enzyme activity in the reaction of formula (III) in the left direction can be measured, for example, by carrying out the reaction of formula (V) and optically measuring the concentration of a quinoneimine pigment formed by the reaction.

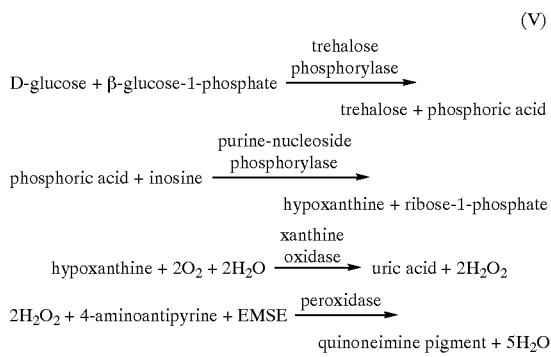

The reaction mixture for the measurement of this enzyme activity is prepared by adding purine-nucleoside phosphorylase, xanthine oxidase, peroxidase, glucose, β-glucose-1-phosphate, inosine, 4-aminoantipyrine, EMSE, etc. to a buffer such as imidazole buffer. The pH of the imidazole buffer is preferably 5.0–8.0, more preferably 6.0–7.0, and the concentration thereof is preferably 10–200 mM, more preferably 50–100 mM.

The concentrations of the substances added to the buffer are as follows: purine-nucleoside phosphorylase, preferably 0.1–10 U/ml, more preferably 1–5 U/ml; xanthine oxidase, preferably 1–50 U/ml, more preferably 5–20 U/ml; peroxidase, preferably 1–50 U/ml; glucose, preferably 5–200 mM, more preferably 20–100 mM; β-glucose-1-phosphate, preferably 5–200 mM, more preferably 20–100 mM; inosine, preferably 0.5–50 mM, more preferably 1–10 mM; 4-aminoantipyrine, preferably 0.5–50 mM, more preferably 1–10 mM; EMSE, preferably 0.5–50 mM, more preferably 1–10 mM.

To the above-described reaction mixture is added a sample containing 1,5-anhydroglucitol, and reaction is carried out at 10–50° C. for 1–20 minutes, preferably at 25–40° C. for 5–15 minutes. The enzyme activity can be determined from the concentration of the quinoneimine pigment formed by the reaction which is determined by measuring the absorbance at 550 nm.

The reagent for quantitative determination of 1,5-anhydroglucitol of the present invention which comprises an enzyme having activity that is inhibited by 1,5-anhydroglucitol in a concentration-dependent manner, a substrate for the enzyme, and a reagent for quantitative determination of a product formed by the enzyme activity is described below.

When trehalase is used as the enzyme having activity that is inhibited by 1,5-anhydroglucitol in a concentration-dependent manner, the substrate is trehalose, and the reagent for the determination of the formed product is that for the determination of D-glucose.

When trehalose phosphorylase is used as the enzyme having activity that is inhibited by 1,5-anhydroglucitol in a concentration-dependent manner, the substrates are trehalose and phosphoric acid, or D-glucose and β-glucose-1-phosphate. The products formed in each reaction are D-glucose and β-glucose-1-phosphate, or trehalose and phosphoric acid, respectively. That is, the reagent for the determination of the formed product is that for the determination of trehalose, phosphoric acid, D-glucose, or β-glucose-1-phosphate.

A reagent for the measurement of trehalase activity comprises trehalose and the reagent for the determination of D-glucose. It may additionally contain a buffer, other enzymes, substrates therefor, and coenzymes, if necessary. A reagent for the measurement of trehalose phosphorylase activity comprises trehalose, phosphoric acid, and the reagent for the determination of D-glucose or the reagent for the determination of β-glucose-1-phosphate; or D-glucose, β-glucose-1-phosphate, and the reagent for the determination of trehalose or the reagent for the determination of phosphoric acid. It may additionally contain a buffer, other enzymes, substrates therefor, and coenzymes, if necessary.

The reagents for the determination of D-glucose, β-glucose-1-phosphate, trehalose, and phosphoric acid respectively comprise substances such as those used in the above-described methods for determining these substances.

A reagent for the elimination of D-glucose comprises substances such as those used in the above-described methods for converting D-glucose into other substances by the use of enzymes.

For example, a reagent for the elimination of D-glucose according to the above method 1) may comprise glucose oxidase, peroxidase, EMSE, and if necessary, the above-mentioned buffer, other enzymes, substrates therefor, and coenzymes. A reagent for the elimination of D-glucose according to the above method 4) may comprise glucokinase, glucose-6-phosphate dehydrogenase, adenosine triphosphatase, adenosine triphosphate, NADP, and if necessary, the above-mentioned buffer, other enzymes, substrates therefor, and coenzymes. The reagent for the elimination of D-glucose may be incorporated with the above-described reagent for the determination of 1,5-anhydroglucitol to make a reagent kit.

The enzymes to be used such as glucose oxidase, glucose dehydrogenase, pyranose oxidase, glucokinase, hexokinase, β-phosphoglucomutase, purine-nucleoside phosphorylase, xanthine oxidase, peroxidase, and adenosine triphosphatase can be obtained as commercial products, or may be prepared by culturing microorganisms capable of producing these enzymes. As the buffers, substrates, coenzymes, substrates for the enzymes, color reagents, fluorescence reagents and luminescence reagents, commercially available ones can be used.

The following Test Example shows an example of the inhibition of the enzyme activity by 1,5-anhydroglucitol, by using trehalase derived from *Rhodococcus globerulus* ATCC 14898.

TEST EXAMPLE 1

(Specificity of inhibition by 1,5-anhydroglucitol)

A reaction mixture was prepared by adding 10 mU/ml trehalase prepared in Reference Example 3, 0.81 mg/ml 4-aminoantipyrine, 1 mg/ml EMSE, 30 U/ml glucose oxidase, 10 U/ml peroxidase, and 1 mM test sugar shown in Table 4 to 100 mM phosphate buffer (pH 7.0). After addition of 10 mg/ml trehalose to the reaction mixture and stirring, the change in absorbance at 550 nm was measured with a spectrophotometer.

The increase in absorbance was measured for 10 minutes after the start of reaction, and the inhibition rate (%) was calculated from the increase in absorbance in the absence of test sugar (A) and that in the presence of 1 mM test sugar (B) according to the following equation:
[(A−B)/A×100]. The results are shown in Table 4.

TABLE 4

| Test sugar (1 mM) | Inhibition (%) |
|---|---|
| 1,5-Anhydroglucitol | 45.0 |
| D-Glucosamine | 0 |
| N-Acetyl-D-glucosamine | 0 |
| D-Mannose | 0.5 |
| D-Galactose | 0.2 |
| D-Fructose | 0 |
| D-Fucose | 0 |
| L-Fucose | 0 |
| D-Xylose | 0 |
| Maltose | 0 |
| Sucrose | 0 |

The activity of trehalase derived from *Rhodococcus globerulus* ATCC 14898 is inhibited specifically by 1,5-anhydroglucitol.

Certain embodiments of the invention are illustrated in the following Examples.

EXAMPLE 1

Determination of 1,5-anhydroglucitol using trehalose phosphorylase derived from *Catellatospora ferruginea* FERM BP-4329

A reaction mixture was prepared by adding 10 mU/ml trehalose phosphorylase derived from *Catellatospora ferruginea* prepared in Reference Example 1, 2.5 U/ml 5-phosphoglucomutase (Beckman Instruments, Inc.), 5 U/ml glucose-6-phosphate dehydrogenase (Sigma Chemical Co.), 10 mM NADP, and a sample containing 1,5-anhydroglucitol at a varied concentration to 100 mM phosphate buffer (pH 7.0). After addition of 10 mg/ml trehalose to the reaction mixture and stirring, the increase in absorbance at 340 nm was measured with a spectrophotometer.

Figure 5:
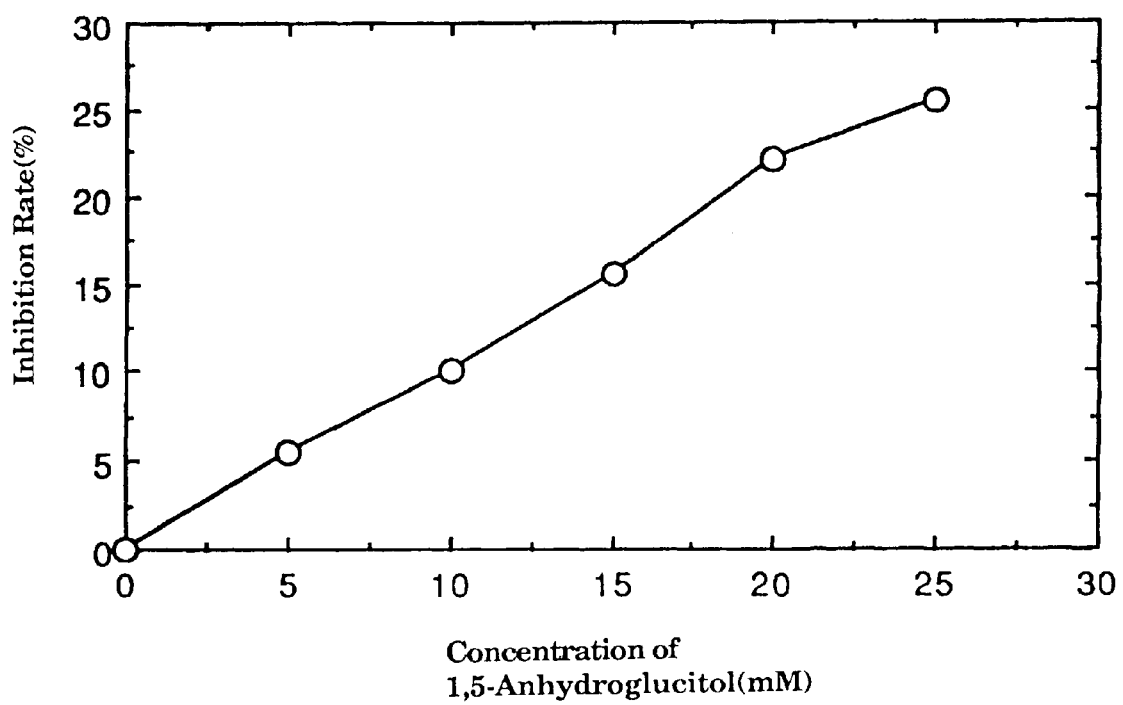
FIG. 5 shows the calibration curve obtained by using as an index the decomposition activity of trehalose phosphorylase derived from Catellatospora ferruginea FERM BP-4329. The numbers on the ordinate indicate the enzyme activity inhibition rate (%) and those on the abscissa indicate the 1,5-anhydroglucitol concentration (mM).

The increase in absorbance was measured for 10 minutes after the start of reaction, and the inhibition rate (%) was calculated from the increase in absorbance in the absence of 1,5-anhydroglucitol (A) and that in the presence of 1,5-anhydroglucitol at each concentration (B) according to the following equation: [(A−B)/A×100]. As shown in FIG. 5, there was a good linear relationship between the inhibition rate and the 1,5-anhydroglucitol concentration, whereby the calibration curve for 1,5-anhydroglucitol was obtained.

EXAMPLE 2

Determination of 1,5-anhydroglucitol using trehalose phosphorylase derived from *Catellatospora ferruginea* FERM BP-4329

A reaction mixture (3 ml) was prepared by adding 10 mU/ml trehalose phosphorylase prepared in Reference Example 1, 50 mM glucose, 2 ml of a kit for the determination of inorganic phosphorus (Kyowa Medex Co., Ltd.), and a sample containing 1,5-anhydroglucitol at a varied concentration to 50 mM imidazole buffer (pH 7.0). After addition of 50 mM β-glucose-1-phosphate to the reaction mixture and stirring, the increase in absorbance at 550 nm was measured with a spectrophotometer.

Figure 6:
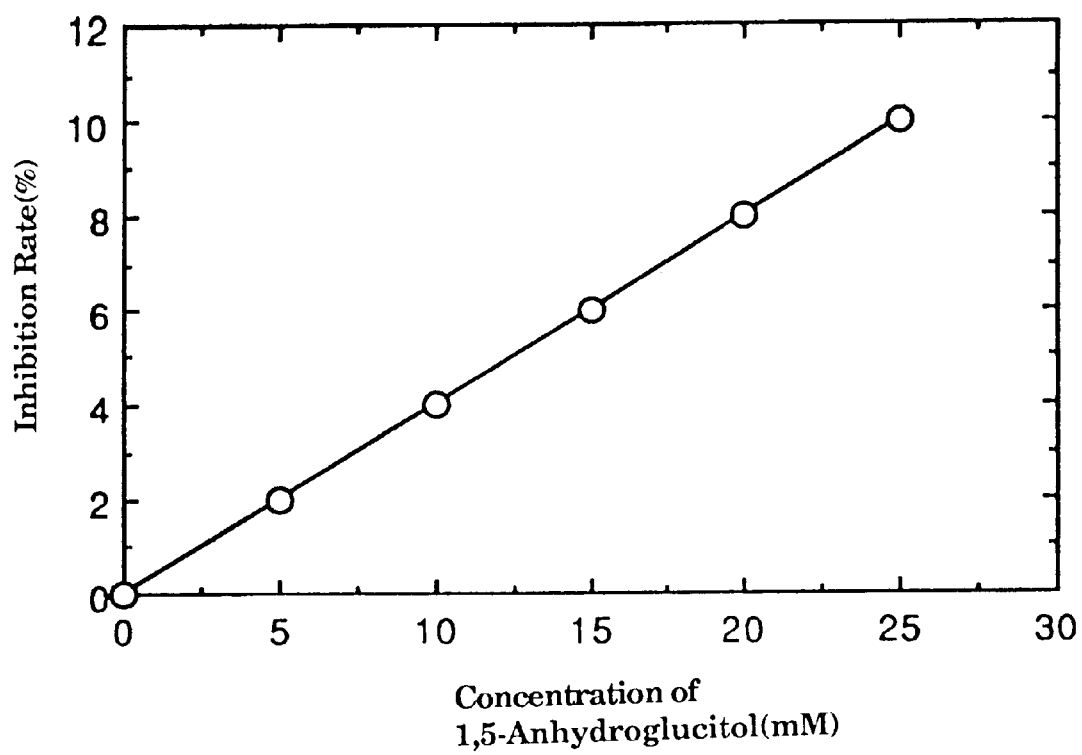
FIG. 6 shows the calibration curve obtained by using as an index the synthesis activity of trehalose phosphorylase derived from Catellatospora ferruginea FERM BP-4329. The numbers on the ordinate indicate the enzyme activity inhibition rate (%) and those on the abscissa indicate the 1,5-anhydroglucitol concentration (mM).

The increase in absorbance was measured for 10 minutes after the start of reaction, and the inhibition rate (%) was calculated in the same manner as in Example 1. As shown in FIG. 6, there was a good linear relationship between the inhibition rate and the 1,5-anhydroglucitol concentration, whereby the calibration curve for 1,5-anhydroglucitol was obtained.

EXAMPLE 3

Determination of 1,5-anhydroglucitol using trehalase derived from *Streptomyces aureofaciens* ATCC 10762

A reaction mixture was prepared by adding 10 mU/ml trehalase prepared in Reference Example 2, 0.81 mg/ml 4-aminoantipyrine, 1 mg/ml EMSE, 30 U/ml glucose oxidase, 10 U/ml peroxidase, and a sample containing 1,5-anhydroglucitol at a varied concentration to 100 mM phosphate buffer (pH 7.0). After addition of 10 mg/ml trehalose to the reaction mixture and stirring, the increase in absorbance at 550 nm was measured with a spectrophotometer.

Figure 7:
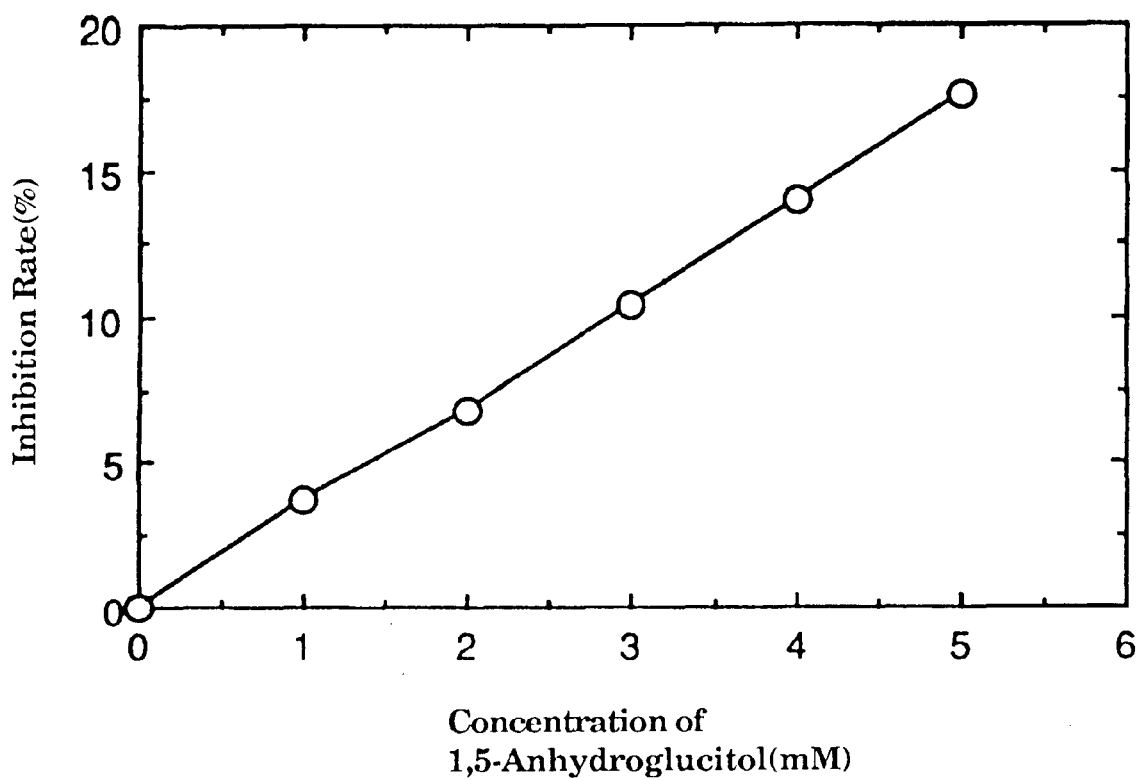
FIG. 7 shows the calibration curve obtained by using as a test enzyme trehalase derived from *Streptomyces aureofaciens* ATCC 10762. The numbers on the ordinate indicate the enzyme activity inhibition rate (%) and those on the abscissa indicate the 1,5-anhydroglucitol concentration (mM).

The increase in absorbance was measured for 10 minutes after the start of reaction, and the inhibition rate (%) was calculated in the same manner as in Example 1. As shown in FIG. 7, there was a good linear relationship between the inhibition rate and the 1,5-anhydroglucitol concentration, whereby the calibration curve for 1,5-anhydroglucitol was obtained.

EXAMPLE 4

Determination of 1,5-anhydroglucitol using trehalase derived from *Rhodococcus globerulus* ATCC 14898

Figure 8:
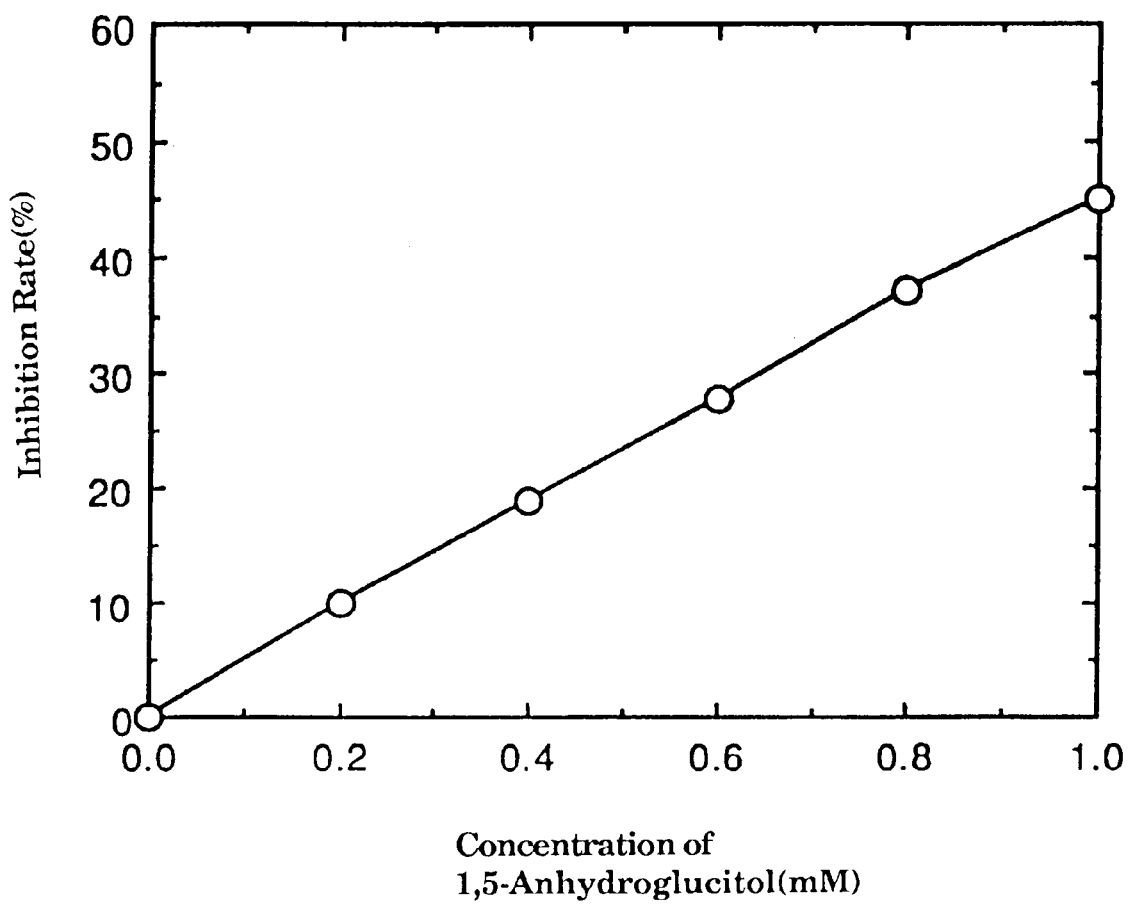
FIG. 8 shows the calibration curve obtained by using as a test enzyme trehalase derived from *Rhodococcus globerulus* ATCC 14898. The numbers on the ordinate indicate the enzyme activity inhibition rate (%) and those on the abscissa indicate the 1,5-anhydroglucitol concentration (mM).

The same procedure as in Example 3 was repeated, except that trehalase derived from *Rhodococcus globerulus* prepared in Reference Example 3 was used. As shown in FIG. 8, there was a good linear relationship between the inhibition rate and the 1,5-anhydroglucitol concentration, whereby the calibration curve for 1,5-anhydroglucitol was obtained.

EXAMPLE 5

Production of trehalase using Nocardia sp. NK-2067

Nocardia sp. NK-2067 was inoculated into 125 ml of a medium (pH 7.2) comprising 1 g/dl sucrose, 0.5 g/dl NZ-amine, 0.2 g/dl peptone, 0.1 g/dl yeast extract and 0.1 g/dl meat extract in a 1-1 Erlenmeyer flask, and cultured with shaking at 30° C. for 48 hours. The resulting culture (125 ml) was inoculated into 2375 ml of a medium having the same composition as above in a 5-1 jar fermentor, and cultured with aeration and stirring at 30° C. for 2 days.

The resulting culture (2.5 l) was centrifuged (12,000×g, 20 minutes) to collect cells. The cells were suspended in 500 ml of 50 mM phosphate buffer (pH 7.0) containing 10% glycerol (hereinafter referred to as GP buffer) and disrupted by using Dynomill (W. A. Bachofen), followed by centrifugation (12,000× g, 20 minutes). To the obtained supernatant was added ammonium sulfate, and the fraction precipitating by 70% saturation with ammonium sulfate was collected and dissolved in a small amount (about 100 ml) of GP buffer. The resulting solution was dialyzed against 5 l of GP buffer for 24 hours. The dialyzed solution was passed through a column (1 L, diameter: 5 cm) of DEAE-Cellulofine (Seikagaku Kogyo Co., Ltd.) pre-equilibrated with GP buffer, whereby trehalase was adsorbed on the column. After the column was washed with the same buffer to remove contaminating proteins, elution was carried out with a concentration gradient of sodium chloride using GP buffers containing 0–1 M sodium chloride. The active fractions eluted with ca. 0.4–0.6 M sodium chloride were combined, and ammonium sulfate was added thereto. The fraction precipitating by 70% saturation with ammonium sulfate was collected by centrifugation (12,000× g, 20 minutes) and dissolved in 50 ml of GP buffer. The resulting solution was dialyzed against 2 l of GP buffer for 24 hours to obtain a purified trehalase preparation.

The specific activity of the enzyme preparation was 21 mU/mg.

EXAMPLE 6

Determination of 1,5-anhydroglucitol using trehalase derived from Nocardia sp. NK-2067

Figure 9:
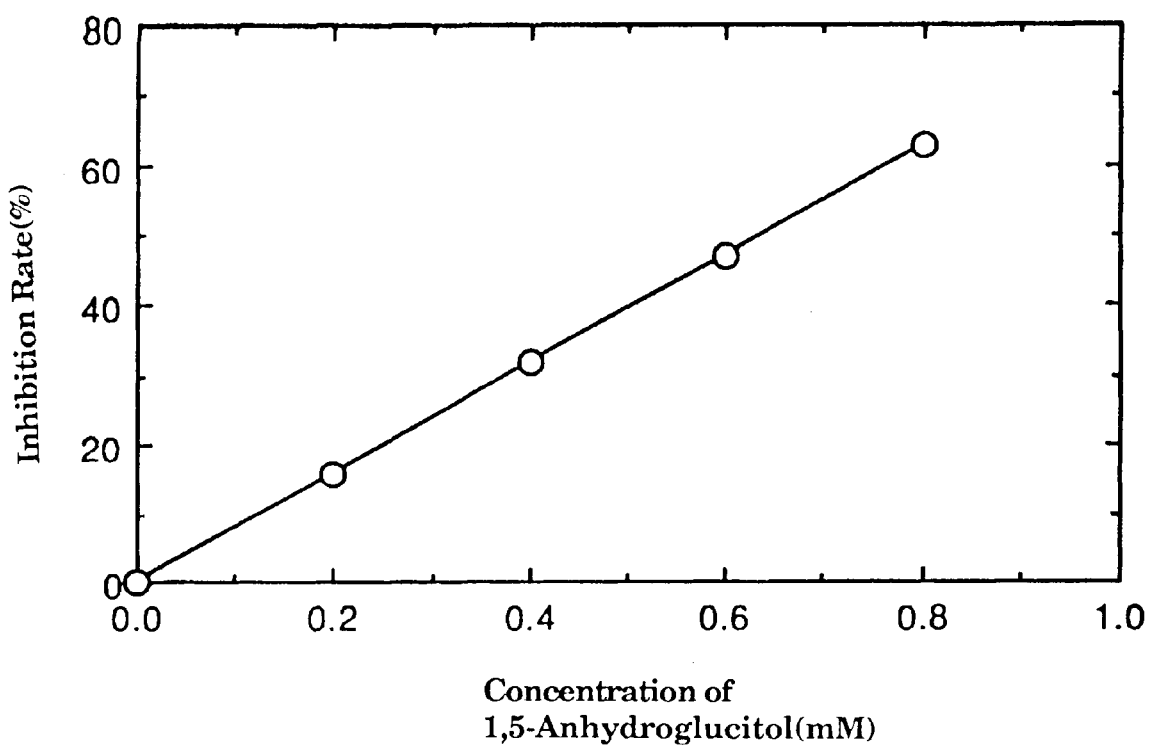
FIG. 9 shows the calibration curve obtained by using as a test enzyme trehalase derived from Nocardia sp. NK-2067. The numbers on the ordinate indicate the enzyme activity inhibition rate (%) and those on the abscissa indicate the 1,5-anhydroglucitol concentration (mM).

The same procedure as in Example 3 was repeated, except that trehalase derived from Nocardia sp. prepared in Example 5 was used. As shown in FIG. 9, there was a good linear relationship between the inhibition rate and the 1,5-anhydroglucitol concentration, whereby the calibration curve for 1,5-anhydroglucitol was obtained.

EXAMPLE 7

A reagent kit for the determination of 1,5-anhydroglucitol consisting of the following Reagents 1, 2 and 3 was prepared.

Reagent 1:

| | |
|---|---|
| Glucose oxidase (derived from *Aspergillus niger*, Toyobo Co., Ltd.) | 30 U/ml |
| Peroxidase (derived from horseradish, Toyobo Co., Ltd.) | 10 U/ml |
| EMSE | 1 mg/ml |
| Phosphate buffer (pH 5.5) | 100 mM |

Reagent 2:

| | |
|---|---|
| Trehalase (prepared in Example 5) | 1 U/ml |
| 4-Aminoantipyrine | 0.8 mg/ml |
| Phosphate buffer (pH 5.5) | 100 mM |

Reagent 3:

| | |
|---|---|
| Trehalose | 2 mM |

EXAMPLE 8

Samples containing 1,5-anhydroglucitol at concentrations ranging from 0 to 500 µg/ml and D-glucose at a concentration of 1 mg/ml were prepared. To 10 µl of each sample was added 300 µl of Reagent 1 prepared in Example 7, and the mixture was incubated at 30° C. for 10 minutes to convert D-glucose into D-glucono-δ-lactone and to simultaneously eliminate the formed hydrogen peroxide. Then, 100 µl of Reagent 2 prepared in Example 7 was added, followed by addition of 10 µl of Reagent 3 prepared in Example 7. The increase in absorbance was measured with an autoanalyzer (Hitachi 7070).

Figure 10:
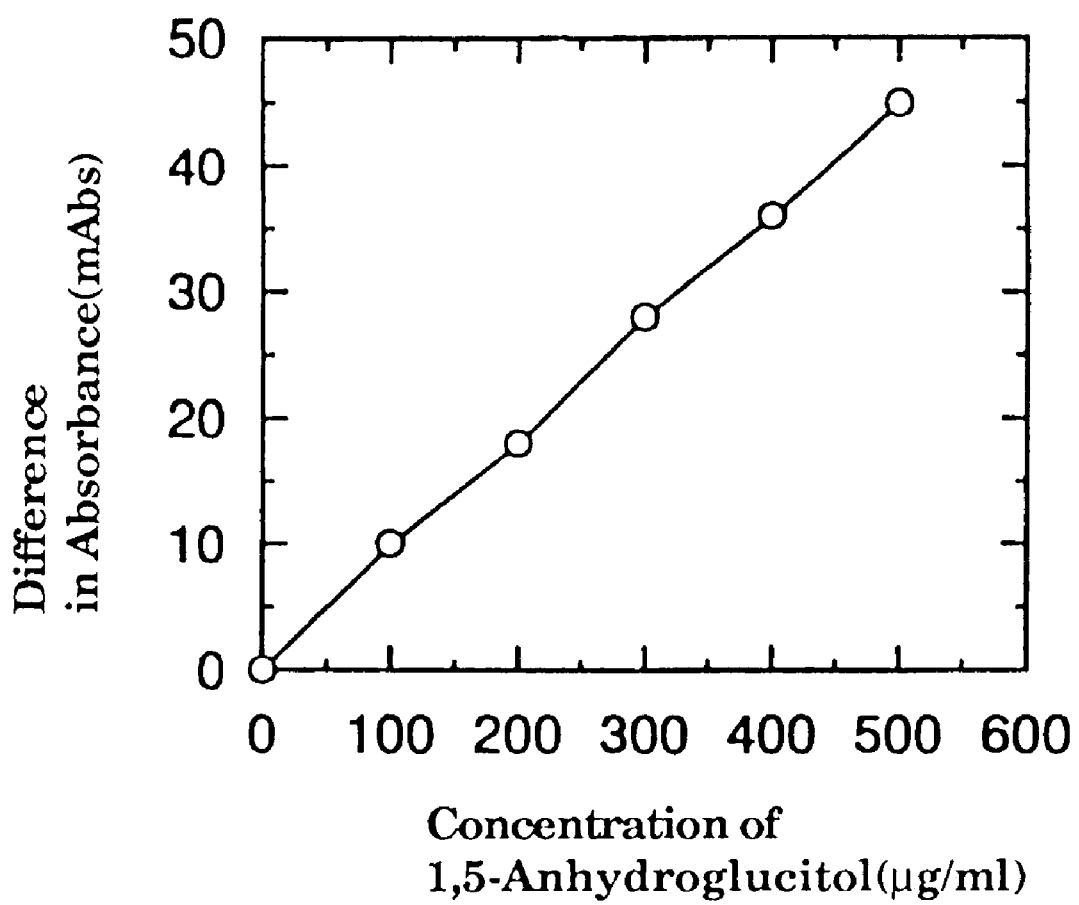
FIG. 10 shows the calibration curve for 1,5-anhydroglucitol in the presence of glucose obtained by using as an index the inhibition rate against trehalase derived from Nocardia sp. NK-2067. The numbers on the ordinate indicate the difference between the absorbance in the absence of 1,5-anhydroglucitol and the absorbance in the presence of 1,5-anhydroglucitol (difference in absorbance), and those on the abscissa indicate the 1,5-anhydroglucitol concentration (µg/ml).

The absorbance in the presence of 1,5-anhydroglucitol at each concentration was subtracted from the absorbance in the absence of 1,5-anhydroglucitol. As shown in FIG. 10, there was a good linear relationship between the obtained absolute value (difference in absorbance) and the 1,5-anhydroglucitol concentration. It was thus demonstrated that the 1,5-anhydroglucitol concentration in samples containing glucose can be determined.

EXAMPLE 9

A reagent kit for the determination of 1,5-anhydroglucitol consisting of the following Reagents 4, 5, 6 and 7 was prepared.

Reagent 4:

| | |
|---|---|
| Glucokinase (derived from *B. stearothermophilus*, Sigma Chemical Co.) | 5 U/ml |
| Adenosine Triphophate | 10 mM |
| MgCl$_2$ | 20 mM |
| Glucose-6-phosphate dehydrogenase (derived from baker's yeast, Sigma Chemical Co.) | 10 U/ml |
| NADP | 10 mM |
| Phosphate buffer (pH 7.0) | 100 mM |

Reagent 5:

| | |
|---|---|
| Adenosine triphosphatase (derived from swine brain, Sigma Chemical Co.) | 3 U/ml |

Reagent 6:

| | |
|---|---|
| Trehalase (Prepared in Example 5) | 1 U/ml |
| Glucose oxidase | 30 U/ml |
| Peroxidase | 10 U/ml |
| 4-Aminoantipyrine | 0.8 mg/ml |
| EMSE | 1 mg/ml |
| Phosphate buffer (pH 7.0) | 100 mM |

Reagent 7:

| | |
|---|---|
| Trehalose | 2 mM |

EXAMPLE 10

Samples containing 1,5-anhydroglucitol at a concentration of 500 µg/ml and D-glucose at concentrations ranging from 1 to 10 mg/ml were prepared. To 10 µl of each sample was added 300 µl of Reagent 9 prepared in Example 9, and the mixture was incubated at 30° C. for 10 minutes. Then, 10 µl of Reagent 5 prepared in Example 9 was added, and the mixture was incubated for 5 minutes to decompose adenosine triphosphate, whereby the glucokinase reaction was stopped. Glucose was converted into D-glucono-δ-lactone-6-phosphate via glucose-6-phosphate through these steps.

To the reaction mixture were added 100 µl of Reagent 6 prepared in Example 9, and then 10 µl of Reagent 7 prepared in Example 9. Reaction was carried out at 30° C. for 10 minutes, and the increase in absorbance was measured with an autoanalyzer (Hitachi 7070).

The difference in absorbance was calculated in the same manner as in Example 8, and the relationship between the obtained values and the glucose concentrations in the samples was studied. As shown in Table 5, the difference in absorbance was constant regardless of the glucose concentrations in the samples. It was thus demonstrated that the 1,5-anhydroglucitol concentration can be determined in the presence of glucose.

TABLE 5

| Concentration of glucose added (mg/ml) | Difference in absorbance (mAbs) |
|---|---|
| 0 | 55 |
| 1.0 | 55 |
| 2.5 | 56 |
| 5.0 | 55 |
| 7.5 | 54 |
| 10.0 | 56 |

EXAMPLE 11

A normal human serum and 1,5-anhydroglucitol-added sera prepared by adding to this normal serum 1,5-anhydroglucitol at concentrations ranging from 0 to 500 μg/ml were used as samples. To 20 μl of each sample was added 300 μl of Reagent 4 prepared in Example 9, and the mixture was incubated at 30° C. for 10 minutes. Then, 10 μl of Reagent 5 prepared in Example 9 was added, followed by incubation for 5 minutes. To the resulting mixture were added 100 μl of Reagent 6 prepared in Example 9, and then 10 μl of Reagent 7 prepared in Example 9. Reaction was carried out at 30° C. for 10 minutes, and the increase in absorbance was measured with an autoanalyzer (Hitachi 7070). Separately, the same procedure as above was carried out on samples containing 0–500 μg/ml 1,5-anhydroglucitol to prepare a calibration curve. The 1,5-anhydroglucitol concentrations in the serum samples were calculated based on the calibration curve. The results are shown in Table 6.

TABLE 6

| 1,5-Anhydroglucitol added (μg/ml) | Found value (μg/ml) | Recovery (%) |
|---|---|---|
| 0 | 25 | — |
| 100 | 124 | 96 |
| 200 | 224 | 96 |
| 300 | 325 | 100 |
| 400 | 426 | 104 |
| 500 | 526 | 104 |

The 1,5-anhydroglucitol concentration in the normal human serum as determined was in close agreement with the value in the literature. The values found for the 1,5-anhydroglucitol-added sera showed the recovery close to theoretical values. It was thus demonstrated that the 1,5-anhydroglucitol concentration in serum can be determined by the method according to the present invention.

REFERENCE EXAMPLE 1

Production of trehalose phosphorylase using *Catellatospora ferruginea* FERM BP-4329

*Catellatospora ferruginea* was inoculated into 300 ml of a medium (pH 7.0) comprising 3 g/dl sucrose, 0.5 g/dl NZ-amine, 0.2 g/dl peptone, 0.1 g/dl yeast extract and 0.1 g/dl meat extract in a 2-1 Erlenmeyer flask, and cultured with shaking at 30° C. for 48 hours. The resulting culture (600 ml) was inoculated into 15 l of a medium having the same composition as above in a 30-1 jar fermentor, and cultured with aeration and stirring at 30° C. for 3 days.

The resulting culture (15 l) was centrifuged (12,000× g, 20 minutes) to collect cells. The cells were suspended in 1000 ml of 200 mM phosphate buffer (pH 7.0) and disrupted by using Dynomill (W. A. Bachofen), followed by centrifugation (12,000× g, 20 minutes). To the obtained supernatant was added ammonium sulfate to 50% saturation, and the formed precipitate was collected and dissolved in a small amount (about 200 ml) of 200 mM phosphate buffer (pH 7.0). The resulting solution was dialyzed against 5 l of the same buffer for 24 hours. The dialyzed solution was heated at 65° C. for 15 minutes, followed by centrifugation (12,000× g, 20 minutes). The obtained supernatant was passed through a column (1 L, diameter: 5 cm) of a gel filtration medium (Toyopearl HW65F, Tosoh Corporation) pre-equilibrated with the same buffer. The active fractions eluted were combined, and ammonium sulfate was added thereto to 50% saturation. The formed precipitate was collected by centrifugation (12,000 r.p.m., 20 minutes) and dissolved in 20 ml of 200 mM phosphate buffer (pH 7.0). The resulting solution was dialyzed against 2 l of the same buffer for 24 hours to obtain a trehalose phosphorylase preparation.

The specific activity of the enzyme preparation was 100 mU/mg.

REFERENCE EXAMPLE 2

Production of trehalase using *Streptomyces aureofaciens* ATCC 10762

*Streptomyces aureofaciens* ATCC 10762 was inoculated into 125 ml of a medium (pH 7.2) comprising 1 g/dl sucrose, 0.5 g/dl NZ-amine, 0.2 g/dl peptone, 0.1 g/dl yeast extract and 0.1 g/dl meat extract in a 1-1 Erlenmeyer flask, and cultured with shaking at 30° C. for 48 hours. The resulting culture (125 ml) was inoculated into 2375 ml of a medium having the same composition as above in a 5-1 jar fermentor, and cultured with aeration and stirring at 30° C. for 2 days.

The resulting culture (2.5 l) was centrifuged (12,000× g, 20 minutes) to collect cells. The cells were suspended in 500 ml of 50 mM phosphate buffer (pH 7.0) containing 10% glycerol (hereinafter referred to as GP buffer) and disrupted by using Dynomill (W. A. Bachofen), followed by centrifugation (12,000× g, 20 minutes). To the obtained supernatant was added ammonium sulfate, and the fraction precipitating by 70% saturation with ammonium sulfate was collected and dissolved in a small amount (about 100 ml) of GP buffer. The resulting solution was dialyzed against 5 l of GP buffer for 24 hours. The dialyzed solution was passed through a column (1 L, diameter: 5 cm) of DEAE-Cellulofine (Seikagaku Kogyo Co., Ltd.) pre-equilibrated with GP buffer, whereby trehalase was adsorbed on the column. After the column was washed with the same buffer to remove contaminating proteins, elution was carried out with a concentration gradient of sodium chloride using GP buffers containing 0–1 M sodium chloride. The active fractions eluted with ca. 0.4–0.6 M sodium chloride were combined, and ammonium sulfate was added thereto. The fraction precipitating by 70% saturation with ammonium sulfate was collected by centrifugation (12,000× g, 20 minutes) and dissolved in 50 ml of GP buffer. The resulting solution was dialyzed against 2 l of GP buffer for 24 hours to obtain a purified trehalase preparation.

The specific activity of the enzyme preparation was 21 mU/mg.

REFERENCE EXAMPLE 3

Production of trehalase using *Rhodococcus globerulus* ATCC 14898

The same procedure as in Reference Example 2 was repeated, except that *Rhodococcus globerulus* ATCC 14898 was used, whereby a purified trehalase preparation was obtained.

The specific activity of the enzyme preparation was 15 mU/mg.

What is claimed is:

1. A method for detecting a disease state in a mammal, comprising the steps of:
    (a) quantitatively determining 1,5-anhydroglucitol in a biological sample, comprising the steps of:
    (i) selecting an enzyme having activity that is inhibited by 1,5-anhydroglucitol in a concentration-dependent manner, wherein said enzyme does not use 1,5-anhydroglucitol as a substrate and has a Ki value of 0.33 mM or less for 1,5-anhydroglucitol,
    (ii) mixing the biological sample with said enzyme, wherein the biological sample is cerebrospinal fluid, blood plasma, serum or urine,
    (iii) thereafter measuring activity of the enzyme, and
    comparing measured enzyme activity with a calibration curve obtained from known amounts of 1,5-anhydroglucitol; and
    (b) determining a disease state of said mammal by comparison of changes in the 1,5-anhydroglucitol level.

2. A method for the quantitative determination of 1,5-anhydroglucitol in a sample, comprising the steps of:
    selecting an enzyme having activity that is inhibited by 1,5-anhydroglucitol in a concentration-dependent manner, wherein said enzyme does not use 1,5-anhydroglucitol as a substrate,
    mixing the sample with said enzyme,
    thereafter measuring activity of the enzyme, and
    comparing the activity with a calibration curve previously obtained from known amounts of 1,5-anhydroglucitol, wherein the enzyme having activity that is inhibited by 1,5-anhydroglucitol in a concentration-dependent manner is trehalase.

3. A method for the quantitative determination of 1,5-anhydroglucitol in a sample, comprising the steps of:
    selecting an enzyme having activity that is inhibited by 1,5-anhydroglucitol in a concentration-dependent manner, wherein said enzyme does not use 1,5-anhydroglucitol as a substrate,
    mixing the sample with said enzyme,
    thereafter measuring activity of the enzyme, and
    comparing the activity with a calibration curve previously obtained from known amounts of 1,5-anhydroglucitol, wherein the enzyme having activity that is inhibited by 1,5-anhydroglucitol in a concentration-dependent manner is trehalose phosphorylase.

4. The purified enzyme trehalase which is obtained from Nocardia sp. NK-2067 (FERM BP-5359), said enzyme having:
    a Ki value of 0.33 mM or less for 1,5-anhydroglucitol;
    a Km value for trehalose of 6.7 mM;
    an optimum pH of 5–6 and stability at a pH range of 5–10, when treated at 50° C. for 30 minutes;
    an optimum temperature of about 45° C. and stability up to 50° C. when treated at pH 5.0 for 30 minutes;
    a molecular weight, as measured by gel filtration, of about 400,000; and
    a substrate specificity for trehalose;
    wherein said enzyme is inhibited by metal chelating agents, SH blocking reagent, hydroxylamine and nickel sulfate.

5. A process for producing trehalase according to claim 4, comprising: culturing, in a medium, a microorganism belonging to the genus Nocardia sp. NK-2067 (FERM BP-5359) and capable of producing the trehalase, and recovering the trehalase from the culture.

6. A kit for quantitative determination of 1,5-anhydroglucitol in a sample comprising:
    an enzyme having activity that is inhibited by 1,5-anhydroglucitol in a concentration-dependent manner and does not use 1,5-anhydroglucitol as a substrate, wherein said enzyme is isolated from said sample prior to use;
    a substrate for the enzyme, wherein said substrate and said enzyme are mutually isolated in said kit prior to use; and
    a reagent for quantitative determination of a product formed by the enzyme activity,
    wherein the components of the kit are within a container and said kit is admixed with the sample to conduct said determination.

7. The method according to claim 2 or 3, wherein the enzyme having activity that is inhibited by 1,5-anhydroglucitol in a concentration-dependent manner has a Ki value of 0.33 mM or less for 1,5-anhydroglucitol.

8. The kit according to claim 6, wherein the enzyme having activity that is inhibited by 1,5-anhydroglucitol in a concentration-dependent manner is trehalase.

9. The kit according to claim 6, wherein the enzyme having activity that is inhibited by 1,5-anhydroglucitol in a concentration-dependent manner is trehalose phosphorylase.

10. The kit according to claim 6, wherein the enzyme having activity that is inhibited by 1,5-anhydroglucitol in a concentration-dependent manner has a Ki value of 0.33 mM or less for 1,5-anhydroglucitol and does not use 1,5-anhydroglucitol as a substrate.

11. The method according to claim 2, wherein the enzyme having activity that is inhibited by 1,5-anhydroglucitol in a concentration-dependent manner is the trehalase derived from Nocardia sp. NK-2067 (FERM BP-5359).

12. The method according to claim 2 or 11, further comprising pre-treating a sample containing D-glucose and 1,5-anhydroglucitol to eliminate D-glucose.

13. The kit according to claim 8 or 10, further comprising a reagent capable of eliminating D-glucose.

14. A kit for quantitative determination of 1,5-anhydroglucitol in a sample comprising:
    an enzyme having activity that is inhibited by 1,5-anhydroglucitol in a concentration-dependent manner,
    a substrate for the enzyme, and
    a reagent for quantitative determination of a product formed by the enzyme activity,
    wherein the enzyme is isolated in said kit from the substrate for the enzyme before use, and wherein the enzyme having activity that is inhibited by 1,5-anhydroglucitol in concentration-dependent manner is the trehalase derived from Nocardia sp. NK-2067 (FERM BP-5359).

15. A kit for quantitative determination of 1,5-anhydroglucitol in a sample comprising:
    an enzyme having activity that is inhibited by 1,5-anhydroglucitol in a concentration-dependent manner and does not use 1,5-anhydroglucitol as a substrate;
    a substrate for the enzyme, wherein said substrate and said enzyme are mutually isolated in said kit prior to use;

a reagent for quantitative determination of a product formed by the enzyme activity; and a known amount of 1,5-anhydroglucitol, wherein said enzyme and said substrate are admixed with the reagent in the presence of the sample or in the presence of said 1,5-anhydroglucitol.

16. The kit according to claim 15, wherein the enzyme having activity that is inhibited by 1,5-anhydroglucitol in a concentration-dependent manner is trehalase.

17. The kit according to claim 15, wherein the enzyme having activity that is inhibited by 1,5-anhydroglucitol in a concentration-dependent manner is trehalose phosphorylase.

18. The kit according to claim 15, wherein the enzyme having activity that is inhibited by 1,5-anhydroglucitol in a concentration-dependent manner has a Ki value of 0.33 mM or less for 1,5-anhydroglucitol and does not use 1,5-anhydroglucitol as a substrate.

* * * * *